United States Patent [19]
Georgi et al.

[11] Patent Number: 4,881,413
[45] Date of Patent: Nov. 21, 1989

[54] BLOOD FLOW DETECTION DEVICE

[75] Inventors: Donald K. Georgi, Wayzata; Andrew X. Basile, Minnetonka; Lloyd E. Graupmann, Plato, all of Minn.

[73] Assignee: Bio-Medicus, Inc., Eden Prairie, Minn.

[21] Appl. No.: 265,410

[22] Filed: Oct. 31, 1988

[51] Int. Cl.⁴ .............................................. G01F 1/58
[52] U.S. Cl. ........................ 73/861.12; 128/691; 128/DIG. 13
[58] Field of Search ....................... 73/861.13, 861.12; 364/413.07; 128/DIG. 13, 691

[56] References Cited

U.S. PATENT DOCUMENTS

| | | | |
|---|---|---|---|
| 2,149,847 | 3/1939 | Kolin | 73/861.13 |
| 2,896,451 | 7/1959 | Rinia | 73/861.15 |
| 3,387,492 | 6/1968 | Mannhert | 73/861.12 |
| 3,633,401 | 1/1972 | Wada | 73/861.12 |
| 4,118,981 | 10/1978 | Cave | 73/861.13 |
| 4,195,515 | 4/1980 | Smoll | 73/861.13 |

OTHER PUBLICATIONS

"Bio-Probe Disposable Blood Flow Monitoring System", Bio-Medicus, 1/87.

Primary Examiner—Joseph A. Orsino
Assistant Examiner—Hollis T. Chen
Attorney, Agent, or Firm—Harold D. Jastram

[57] ABSTRACT

A blood flow monitoring system employing a disposable sensor for directing a flow of blood through an electromagnetic field to generate a voltage proportional to the flow of blood through the electromagnetic field. The flow detection system employs a disposable sensor having a lumen with a constricted cross-sectional area adapted to interact with an electromagnetic field to detect blood flow and in an enhanced variation includes an electromagnetic field focusing device for enhancing the electromagnetic field to focus the electromagnetic field across the path of blood flow through the constricted section of the lumen to intensify the voltage generated by the blood flow through the intensified electromagnetic field.

35 Claims, 5 Drawing Sheets

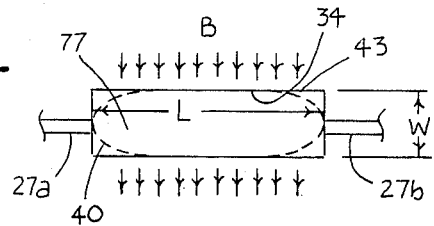
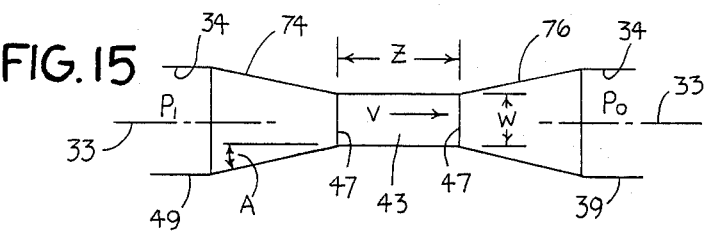
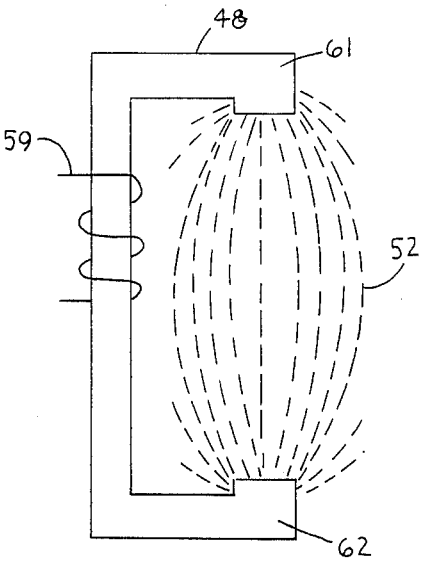
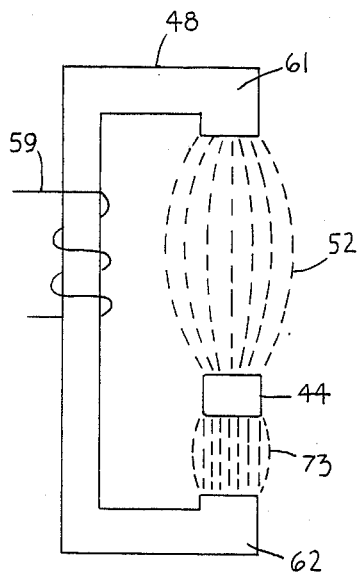
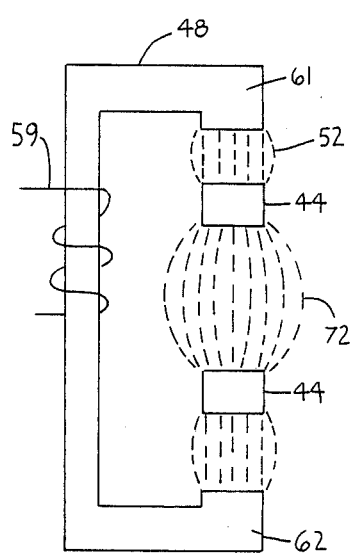
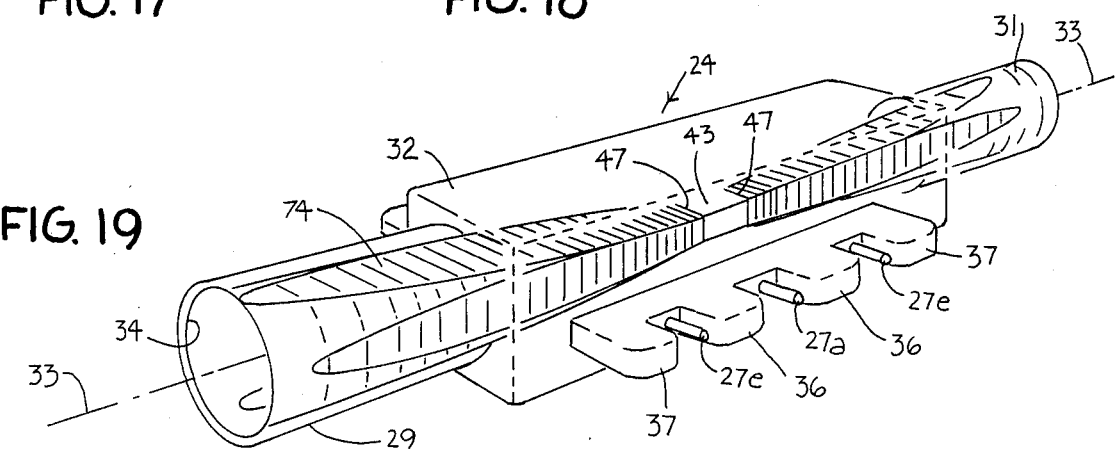

BLOOD FLOW DETECTION DEVICE

BACKGROUND OF THE INVENTION

Current medical practice commonly employs the procedure for surgical correction of diseases of the heart, lungs and liver. Many of these surgical procedures involve massive interruption or disruption of the blood flow of the patient. These procedures frequently require support of the normal cardiovascular function of a patient. Such involvement might be necessary where the surgical procedure involves repair of various heart and vascular organs. During open heart surgery, as an example, a surgeon needs a procedure for insuring a constant flow of blood to the patient while the surgery is being performed on the heart, including the valves and blood vessels of the heart. In such surgery, blood flow support is a common procedure used to insure that adequate blood flow is sustained in the patient's body in order to maintain vital organ functions.

Organ transplant surgery also has become a common medical practice which requires the interruption or disruption of the normal blood flow in a patient. Success of organ transplant of kidneys, liver and the heart requires successful sustaining of the normal blood flow of a patient. This blood flow interruption is sufficiently critical that common surgical procedures require that blood flow assistance to the patient be utilized during the procedure.

The ancillary blood flow assistance to the patient normally involves a blood flow pump used to replace or assist the function of the heart during the course of the procedure. Such blood flow assist requires that the blood flow be monitored at all times during the procedure to insure that the proper flow of blood is occurring in the cardiovascular system to prevent unnecessary complications for the patient and to insure adequate blood flow to vital organs during the course of surgical procedure.

One of the vital conditions which must be observed throughout the course of supplementary assistance to the cardiovascular function of a patient is a monitoring of the blood flow in the patient's body as the patient's system is being assisted by an artificial blood pump. A part of this entire system involves a blood flow monitoring system capable of sensitive and continuous monitoring of the blood flow from the pump assist even as the flow rates of the assistance to the patient are at relatively low levels.

The use of electromagnetic flow meters to measure blood flow is known in the medical arts and the basic concept of such measurement was described in U.S. Pat. No. 2,149,847. Because of the composition of blood, it is well known that passing a volume of blood, either in a tube or in a blood vessel at right angles to an established magnetic field will result in the production of an electromotive force (EMF) or induced voltage which is produced in a direction mutually perpendicular to the magnetic field and the direction of the blood flow. As indicated, the blood has the characteristics of a moving conductor and acts the same as passing an electrical wire conductor through a magnetic field. Voltage is generated in a fixed cross-sectional area which is proportional to the average velocity of flow of the blood resulting in a measure of the volume rate of flow of the blood through the tube or blood vessel. This voltage can be sensed by electrodes positioned at diametrically opposite points along the tube or lumen, when the electrode tips in contact with the flowing blood are positioned perpendicular to the direction of the magnetic field.

An important feature of the prior art involves the positioning of the electrodes, magnetic structure, and the blood flow at a fixed pre-determined relationship in order to maintain an accurate calibration of the blood flow. Past practice has dictated that the assembled tubes, electrodes and magnetic structure be constructed as a unitary assembly which insures the proper measurement of blood flow. This unitary structure incorporates several serious disadvantages in the practice of medicine since it presents problems of sterilization of the blood flow measuring device itself as well as creating limitations to blood flow-rate sensitivity capabilities.

Ideally, a flow monitoring system should include a method whereby the sensing unit immediately in contact with the patient's blood should be disposable so that each patient can be provided with a flow detection unit which is completely sterile and is not merely a unit which has been subsequently cleaned after previous surgical procedures. Cleaning such units presents serious contamination problems since the success of an operation may be based upon the quality of the sterilization and cleanliness of apparatus used during the surgical procedure. Therefore, it is common in surgical procedures to use newly manufactured and sterilized units which are then discarded after each surgical procedure. This insures maximum sterilization of the implements used during the course of the procedure and eliminates, as much as possible, the likelihood of transmission of communicable diseases and other infections from patient to patient. Use of a disposable flow device greatly enhances the likelihood of success of the surgical procedure.

The devices which monitor blood flow frequently involve electrical terminals, conduits, similar materials, and geometrics which are extremely difficult to sterilize and which, if they are sterilized, are totally dependent on the skill and care of a number of participants in the sterilization process. Not only does the sterilization depend upon the initial cleaning process but it also depends upon the type of sterilization practice employed to clean the device. Further, following initial sterilization, the successful use of such reusable devices depends upon the care with which the unit is stored. Consequently, disposable units which are discarded after each surgical procedure are likely to greatly enhance the success of a surgical procedure.

SUMMARY OF THE INVENTION

The present invention is directed to an improvement in systems used for measuring the blood flow and employing electromagnetic techniques to monitor such blood flow. The system employs a sensor which directs blood past an electromagnetic field where the blood flow is detected as the blood generates an electromotive force as it passes through the electromagnetic field. A special characteristic of the present invention is the employment of an electromagnetic field focusing device in cooperation with a sensor which permits precise control of the electromagnetic field and also a method of amplification of the rate of blood-flow through said magnetic field by incorporating a hydrodynamically shaped lumen, which in combination maximize the sensitivity of the entire system and also minimize the consequence of "noise" inherent in the detection system. The strength of the induced voltage detected by the electrical terminals as the augmented blood-flow flows through the intensified electromagnetic field increases the sensitivity of the device. Increased sensitivity of the device made possible by the electromagnetic focusing characteristics and augmented flow dramatically improves the sensitivity of the system and permits detection and measurement of very low rates of flow of blood through an extracorporeal system designed to assist the natural cardiovascular function of a patient.

One version of the blood flow monitoring system employs a disposable sensor which directs blood through an electromagnetic field where the blood generates an induced voltage as it flows through the electromagnetic field. The disposable sensor employs electrodes which are precisely positioned at right angles to the blood flow to detect the induced voltage generated by the blood flow through the electromagnetic field.

In order to intensify the sensitivity of the system in detecting low rates of blood flow, a magnetic field focusing device is positioned either within or about the sensor in a manner to focus the electromagnetic field across the lumen of the sensor to enhance the sensitivity of the monitoring system. The sensor employs a lumen which is specifically constructed to maximize the flow past and through the magnetic field in order to intensify and increase the induced voltage generated as the blood flows through the field.

The preferred embodiment of the disposable sensor or insert provides a lumen which is constricted in cross-sectional area in the zone where the blood is directed through the electromagnetic field. The electromagnetic field focusing device is positioned between the poles of an electromagnet to focus the electromagnetic field generated between the poles of the magnet across the constricted lumen of the sensor. This focusing is used in order to increase the strength of the electromagnetic field at the constricted section of the lumen so the blood flows through the electromagnetic field at a greater velocity and thereby generates a higher induced voltage. Electrodes are mounted in the disposable insert at right angles to the electromagnetic field and at right angles to the flow of blood through the sensor. The electrodes or male terminals are at right angles to an electromagnetic field which is generated by an electromagnet. The male terminals of the sensor in one variation of the invention are adapted to engage parallel post terminals mounted in a tray which is a part of a transducer. The core of an electromagnetic generating means is mounted and a part of a transducer which provides the electromagnetic field for the system.

In a preferred embodiment of the invention, the lumen is constricted in a section of the sensor located in the electromagnetic field. The cross-section of this constricted section in the invention is an improvement over a typical lumen of circular cross-section where the width and height are equal, to one in this invention where the cross-section has a length greater than its width. Preferably this cross-sectional area is elliptical although a rectangular or modified rectangular shape is also effective.

DESCRIPTION OF THE DRAWINGS

For a more complete understanding of the invention, reference should be made to the accompanying drawings in which:

FIG. 14 is a representation of cross-sections of a lumen of a sensor illustrated in FIG. 2 of the drawings;

FIG. 15 is a diagrammatic representation of a lumen of a sensor taken along a longitudinal center line of a sensor as illustrated in FIG. 2 of the drawings;

FIG. 16 is a representation of an electromagnetic core illustrating an electromagnetic field between the poles of a magnetic core without a focusing device;

FIG. 17 is a diagrammatic illustration of an electromagnetic core illustrating an electromagnetic field between the poles of the magnetic core with a single field focusing device;

FIG. 18 is a diagrammatic representation of a magnetic core illustrating a magnetic field between the poles of the magnetic core employing two focusing devices located in the field between the poles of the core;

FIG. 19 is a perspective view of a sensor of a type illustrated in FIG. 2 of the drawings but illustrated in perspective view to emphasize the lumen of the sensor where the sensor is constructed of transparent material.

DETAILED DESCRIPTION OF THE INVENTION

Figure 1:
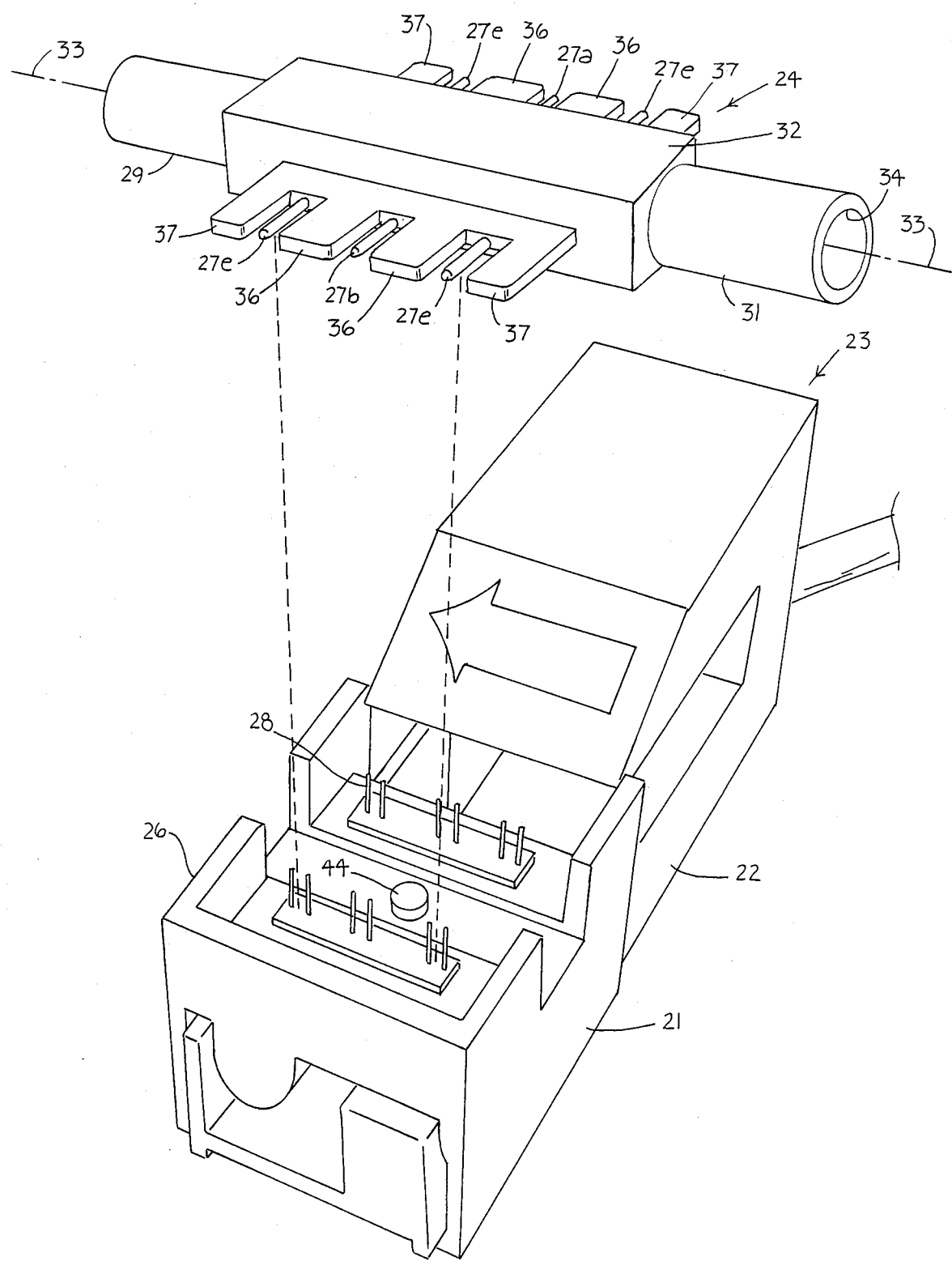
FIG. 1 is a partially exploded perspective view of a transducer, tray and a sensor.
Figure 2:
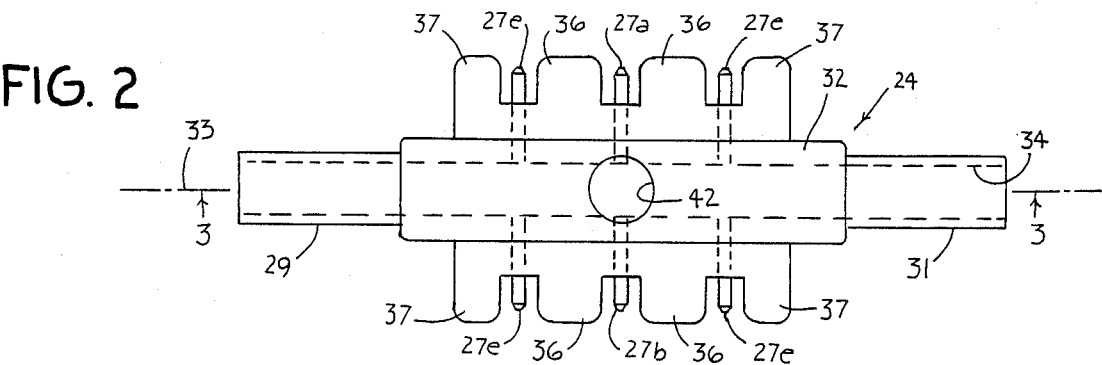
FIG. 2 is a plan view of a sensor.
Figure 8:
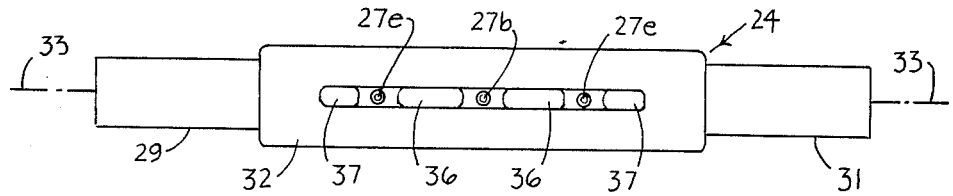
FIG. 8 is a front view of FIG. 2 of the drawings illustrating a sensor.

Refer first to FIG. of the drawings which illustrates a blood flow meter assembly illustrated in a partially exploded perspective view. A tray assembly 21 is mounted on a slide 22 so that the tray assembly 21 moves along the slide 22 to engage a transducer 23. A sensor 24 which is also illustrated in greater detail in FIGS. 2, 8 and 19, is adapted to engage retainer walls 26 of tray 21. The transducer 23 and tray 21 are illustrated in FIG. 1 in the open or unengaged position. The sensor 24 is adapted to be inserted into the tray 21 so that male terminals 27 engage slide terminals 28 on the tray 21.

The sensor 24 has nipples 29 and 31 extending from either end of a body portion 32. The male terminals are electrical terminals which extend perpendicular to a longitudinal axis 33 which extends along a lumen 34 of the sensor 24. The lumen 34 extends along the entire length of the sensor 24 from nipple 31 through nipple 29.

Male electrical terminals 27 are mounted in the body 32 of the sensor 24 perpendicular to the longitudinal axis 33 and, therefore, perpendicular to the lumen 34 of sensor 24. This relationship will be more fully explained in connection with a description of FIGS. 2, 3, 4 and 5 of the drawings.

On opposite sides of the body 32, and separating the male electrical terminals 27 are fins 36. These fins are positioned between male electrical terminals 27 to provide electrical isolation for the terminals 27 and also to assist in the positioning of the sensor 24 in the tray 21.

Also extending perpendicular to the longitudinal axis 33 of lumen 34 are end fins 37 which also act as locators for the relative positioning of sensor 24 in the tray 21. End fins 37, however, are specifically designed to engage wall 26 of tray 21 to securely position the sensor 24 within the walls 26 of tray 21 to prevent longitudinal movement of the sensor 24 along its longitudinal axis 33 when the sensor 24 is placed into engagement with the tray 21. The male electrical terminals 27 are designed to engage slide terminals 28 so that each pair of slide terminals 28 engage a corresponding male electrical terminal 27 when sensor 24 is mounted on tray 21.

Figure 9:
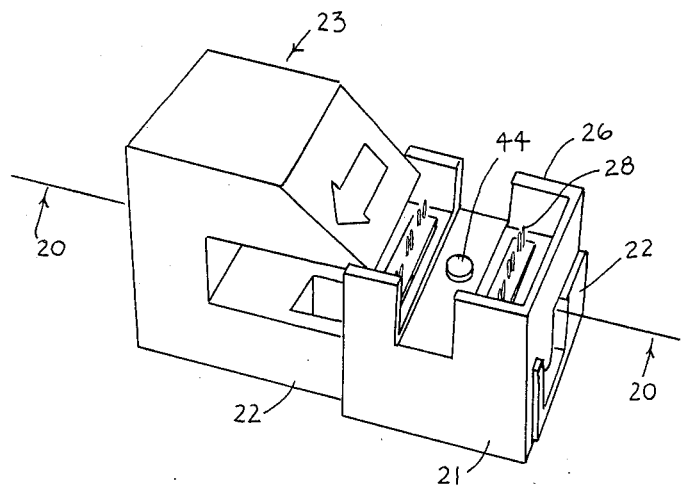
FIG. 9 is a perspective view of a transducer and tray in an open position and without a sensor.
Figure 10:
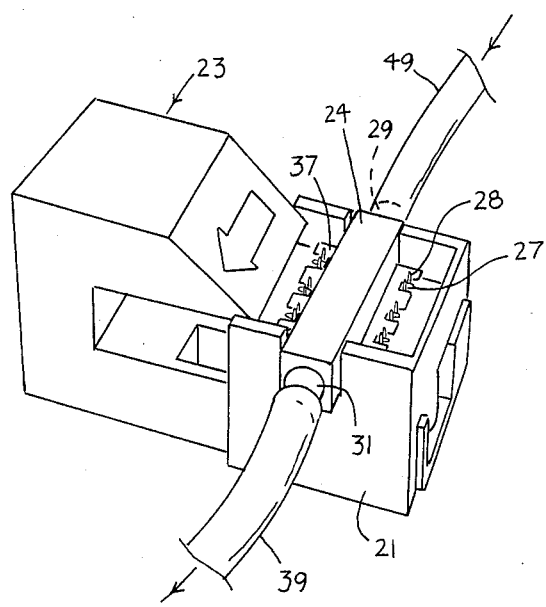
FIG. 10 is a perspective view of a transducer, tray and engaged sensor.
Figure 11:
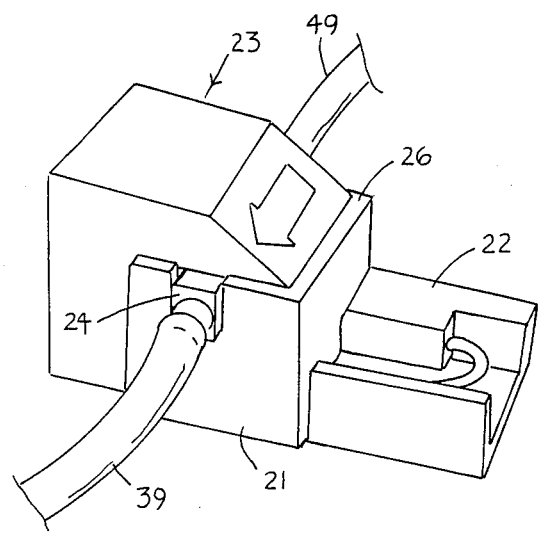
FIG. 11 is a perspective view of a transducer and tray closed on a sensor.

Refer now to FIGS. 9, 10 and 11 of the drawings which are a series of three drawings illustrating the manner in which sensor 24 mechanically engages slide tray 21 and is positioned in transducer 23. In FIG. 9 of the drawings, the transducer 23 and tray 21 are shown in the open or extended position. In this position, tray 21 is disengaged from transducer 23 and is extended at a maximum distance along slides 22 to disengage the tray 21 from transducer 23.

FIG. 10 again illustrates the transducer 23 and the tray 21 in the open or extended position but in this FIG., the sensor 24 has been positioned on tray 21 within the walls 26. It is noted that in this FIG. 10, the end fins 37 engage the inside 38 of walls 26. End fins 37 at either end of body portion 32 of sensor 24 engage the inside 38 of wall 26 to prevent longitudinal movement of the sensor 24 when properly positioned on tray 21.

Also, when sensor 24 is positioned within the walls 26 of tray 21, the male electrical terminals 27 are in engagement with the slide terminals 28 in order to establish an electrical circuit between sensor 24 and electrical systems in slide tray 21 and transducer 23. This electrical system and the related connections will be more fully explained in connection with an explanation of FIG. 12 of the drawings.

Figure 20:
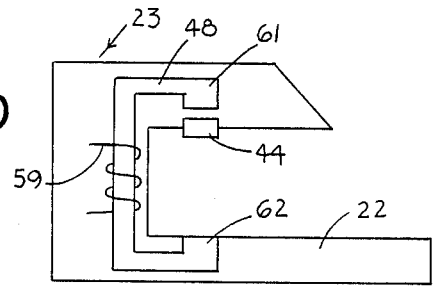
FIG. 20 is a cross-sectional view taken along line 20—20 of FIG. 9 showing an electromagnet in the transducer and further illustrating a focus device mounted in the transducer.

After the sensor 24 has been positioned on tray 21, the tray 21 is moved along slide 22 into engagement with transducer 23 so that the transducer 23 closes upon tray 21. This closed position or condition between the transducer 23 and the slide tray 21 is illustrated in FIG. 11 of the drawings. In this position, the sensor 24 is placed into the electromagnet which will also be described in connection with an explanation of FIGS. 12 and 20 of the drawings so that blood can be directed through the sensor 24 through conduits or tubes 49 and 39. In this closed position, the transducer 23, tray 21 and sensor 24 are now in a mechanical position which permits a functioning of the electrical system necessary to monitor the flow of blood in a patient's cardiovascular system when the patient's cardiovascular system is being supported by a blood pump of the type which is used during surgery involving the cardiovascular system.

Refer next to FIG. 2 of the drawings which illustrates the Sensor 24 in a plan view. Sensor 24 is preferably constructed of a biocompatible plastic material such as acrylic, polyurethane, polycarbonate or polysulfone. Preferably this material is a transparent nonconductive and nonmagnetic material for ready inspection and quality control and one that can be molded in molds commonly used for preparing such products. Male electrical leads are generally designated by numeral 27. All of the leads designated by the numeral 27 are imbedded in the body 32 of the sensor 24 in exactly the same fashion. The different male terminals, however, have different electrical functions and consequently the various male terminals 27 have been designated in FIG. 2 of the drawings with different designations to indicate their differing electrical function. From a mechanical point of view, the male electrical leads or terminals 27 are mechanically positioned and imbedded in the body 32 of the sensor 24 in exactly the same fashion. Male terminals 27a and 27b, however, serve a different electrical function from terminals 27e. Terminals 27e are electrical terminals which provide an electrical ground for the electrical system and will be more fully explained in connection with the operation of the electrical circuit illustrated in FIG. 12 of the drawings.

Electrical male terminals 27a and 27b are designed to pick up or sense the induced voltage generated by blood flow through lumen 34 as the blood moves through an electromagnetic field. This also will be more fully explained in connection with a description of FIG. 12 and also FIGS. 16, 17 and 18 of the drawings.

Fins 37 of the sensor 24 are positioned on either side of the body 32 and are perpendicular to the body. The fins 37 ensure that the sensor 24 are properly oriented in the tray so that the terminals 27e, 27a and 27b properly engage the slide terminals 28.

As indicated, fins 36 act as electrical insulators or means for electrically isolating the male terminals 27 from each other as well as physically protecting the male terminals from mechanical damage while the sensors 24 are being stored and used.

All of the male terminals 27, extend perpendicular to the longitudinal axis 33 of the sensor 24 and, therefore, perpendicular to the longitudinal axis 33 of the lumen 34. This is illustrated in FIG. 2 of the drawings where it is apparent that all of the male terminals 27 are in communication with lumen 34.

Figure 6:
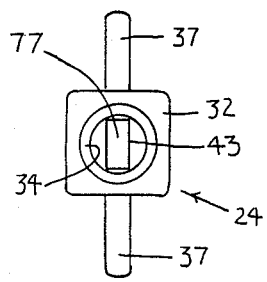
FIG. 6 is a right end view of FIG. 2 of the drawings.
Figure 7:
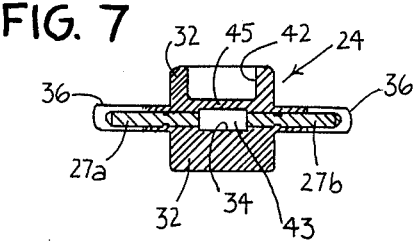
FIG. 7 is a cross-sectional view taken along line of FIG. 4 of the drawings.

The positioning of fins 37 and also fins 36 which are in the same plane as fins 37, is illustrated in both FIGS. 6 and 7 of the drawings where it is apparent that fins 37 on either side of the body 32 of sensor 24 lie in the same plane and are perpendicular to the longitudinal axis 33 of the lumen 34. Also, it will be apparent from a reference to FIG. 7 of the drawings that the male terminals 27 and, as noted in FIG. 7, the voltage sensing terminals 27a and 27b also lie in the same plane as the fins 36. These terminals 27a and 27b (and also male terminals 27e) lie in a common plane and perpendicular to the lumen 34 of the sensor 24.

It is specifically noted at this point that lumen 34 at the location of the male terminals 27a and 27b is no longer circular in nature as it is in the nipples or input section 29 and output section 31 but is constricted and has a greater length L of cross section area than width W to maximize induced voltage as is observed by reviewing FIGS. 14 of the drawings where one variation of the cross-sectional shape of lumen 34 is illustrated.

Referring next to FIG. 8 of the drawings it will be apparent that the fins 36 and 37 lie in the same plane and perpendicular to the body 32 of sensor 24. It is noted in this FIG. that male terminals 27e and 27b are also in the plane of the fins 36 and 37 and also perpendicular to the body of the sensor 24.

Next, refer to FIGS. 2 and 7 of the drawings where there is illustrated a cavity 42 in the body 32 of sensor 24, which approaches lumen 34 in depth but is maintained separate by gland 45. This cavity in one version of the invention is an important feature of the invention. Cavity 42 is located in the body 32 of the sensor 24 in a position located in a central or constricted section 43 of the lumen 34. Cavity 42 is adapted to accommodate a magnetic material designed to focus a magnetic field across the central portion 43 of lumen 34 in order to focus a magnetic field which is directed perpendicular to the longitudinal axis 33 of lumen 34 as blood flows through lumen 34 past the cavity 42. Reference is specifically directed to FIG. 4 of the drawings where it is noted that cavity 42 is located directly in association with the central portion 43 of lumen 34.

Disposable sensor 24 is uniquely adapted to take advantage of the classical laws of induction which involve the movement of a conductor in a magnetic field which generates a voltage proportional to the velocity of that conductor with reference to the magnetic field, and also proportional to the length of the conductor within that field. In the application of this law in this invention, blood acts as the moving conductor as it flows through lumen 34 through the central portion 43 along length Z of the lumen 34 and exits from the sensor 24. Blood in this case is the conductive liquid and is the conductor. A voltage is generated by the movement of the blood and is directly proportional to the average blood velocity as it passes through the various portions of the lumen 34. The length of the "liquid" conductor is equivalent to the length L of the cross-sectional area of the constricted section 43 of lumen 34 and since this length also contributes to voltage generation in direct proportion to its magnitude an embodiment of this invention is to maximize this length L at the expense of the width W of the cross-sectional area of the constricted section of lumen 34.

Cavity 42 of the sensor 24 is provided as a means to accommodate the presence of a magnetic device 44 for focusing the magnetic field across the central portion 43 of lumen 34 in order to intensify and control the voltage generated by the movement of the blood through lumen 34. Cavity 42 has a size where the dimensions of the cavity perpendicular to the blood flow as viewed in FIG. 2 of the drawing is greater than the length L of the cross-sectional area 43 shown in FIG. 14 of the drawing. This phenomenon will be more fully explained hereinafter.

Figure 3:
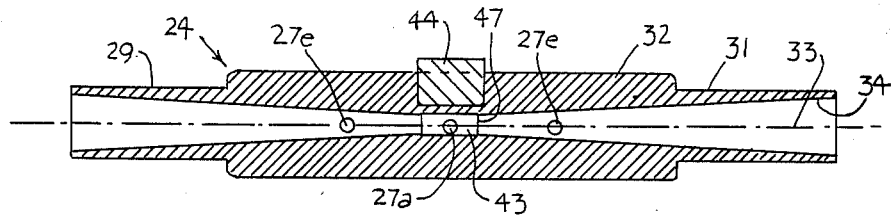
FIG. 3 is a cross-sectional view taken along line 3—3 of FIG. 2 of the drawings and showing an electromagnetic field focusing element.
Figure 4:
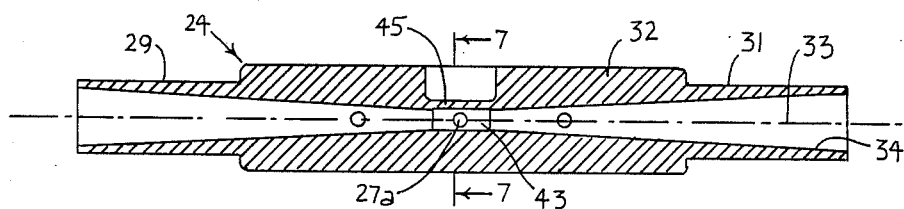
FIG. 4 is an alternate embodiment of FIG. 4 showing a sensor without a focusing element.
Figure 5:
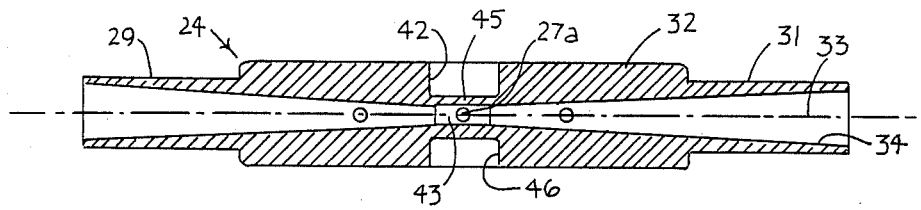
FIG. 5 is an alternate embodiment of FIG. 4 which illustrates a sensor employing two focusing cavities.

While FIGS. 7 and 4 illustrate a cavity 42 which employs a single cavity for accommodation of a single focusing element 44 (see FIG. 3 of the drawings), the sensor 24 may also be constructed to include two diametrically opposite cavities 42 and 46 as illustrated in FIG. 5 of the drawings. In one version of the invention, the cavities are cylindrical in shape as illustrated in FIGS. 2 and 3 of the drawings. Other shapes are contemplated. The central axis of the cylindrical cavity is perpendicular to the blood flow through the lumen 34 and also perpendicular to terminals 27a and 27b. These cavities 42 and 46 are designed to accommodate a focusing device 44 so that a magnetic field which is directed perpendicular to the longitudinal axis 33 of the sensor 24 will be controlled and directed in a controlled manner across the central portion 43 of lumen 34 to intensify and increase the voltage which is generated as blood is flowing through lumen 34 perpendicular to a magnetic field focused by focusing device 44 and also perpendicular to male terminals 27a and 27b (see FIG. 2 of the drawings).

Focusing device 44 may be any magnetically permeable material which is capable of focusing an electromagnetic field in the region of the central portion 43 of lumen 34. Typical examples of such a focusing device would be iron, cobalt, nickel or other metals or compounds well understood which are capable of focusing a magnetic field.

While cavity 42 and cavity 46 are illustrated in the plan view drawings (FIG. 2) as being circular in nature, a circular cavity is not an absolutely necessary requirement of the present invention. The shape of cavities 42 and 46 can be any shape which may be utilized to appropriately focus a magnetic field across (perpendicular to) the lumen 34 in order to take advantage of the conductivity characteristics of blood flowing through lumen 34. While cavity 42 is illustrated as cylindrical in shape, a cylindrical shape is not an absolutely necessary requirement. The shape of cavities 42 and 46 may be any shape or contour.

Preferably, cavities 42 and 46 are shown as having sufficient diameter or cross-sectional size in order to overlap the length L of the central portion 43 of lumen 34. Preferably, the dimensions of cavity 42 are at least the same dimensional size as the distance L of central portion 43 or slightly larger. The cavity 42 in the drawings are shown to be slightly larger than the length of the central or constricted section 43 and is the preferred configuration for the invention. A cavity 42 smaller than the length L is also contemplated.

Figure 12:
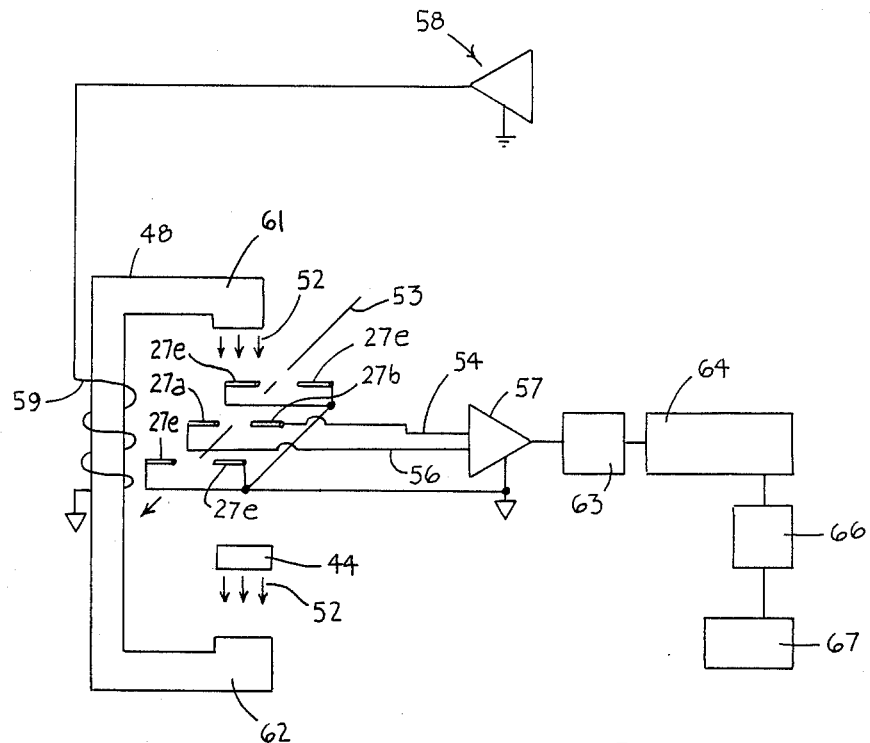
FIG. 12 is a block diagram illustrating the electrical characteristics of the blood flow monitoring system

In operation, the sensor 24 is uniquely adapted to take advantage of well-known principles of generation of currents in electromagnetic fields. The sensor is adapted to be inserted as illustrated in FIG. 10 of the drawings into a tray assembly 21 where the sensor 24 engages the tray and becomes a part of an electrical system designed for sensing a electromotive force generated as a result of blood flow through lumen 34 and past male terminals 27a and 27b of sensor 24. The electrical system is illustrated in FIG. 12 of the drawings.

In operation, as blood flows through the sensor 24 which is mounted in tray assembly 21, the movement of the blood through lumen 34 past terminals 27a and 27b and through an electromagnetic field focused perpendicular to the longitudinal axis 33 of lumen 34 will generate a voltage as the blood flows past the male terminals 27a and 27b. The blood induces this voltage because of the conductive nature of blood flow through an electromagnetic field focused by focus device 44.

The electromotive force induced by the flow of blood through a magnetic field in lumen 34 is picked up by male terminals 27a and 27b. Reference to FIGS. 9, 10 and 11 will more readily clarify the function of the sensor 24. In one version of the invention, a magnetic slug or device 44 is positioned in tray assembly 21 between the slide terminals 28. Slide 21 is shown in FIG. 9 in the open position and unengaged with the transducer 23. In this particular conversion of the invention, device 44 is the focusing device adapted to focus the electromagnetic field which is generated by an electromagnetic core as illustrated in FIG. 16 of the drawings.

The sensor 24 is positioned above the tray 21 (as illustrated in FIG. 1 of the drawings) and is inserted into position in tray 21 as illustrated in FIG. 10 of the drawings. In this position, the cavity 42 is positioned over focus device 44 which is positioned in cavity 42 of the body 32 of sensor 24.

In the position illustrated in FIG. 10 of the drawings, the sensor 24 is positioned on slide 21 so that all of the male terminals 27 engage the slide terminals 28. When the sensor 24 is positioned as illustrated in FIG. 10 of the drawings, tubes 39 and 49 are attached to the nipples 29 and 31 of sensor 24. Tubes 39 and 49 are adapted to direct blood through the sensor 24 and, therefore, through the lumen 34 of sensor 24. Blood flows in the arrow direction from line or tube 49 through the sensor 24 and out tube 39 as illustrated in FIG. 10 of the drawings.

After the sensor 24 has been positioned in slide tray or slide assembly 21, the tray assembly 21 is moved into engagement with the transducer 23 and is positioned as illustrated in FIG. 11 of the drawings. In this position, the sensor 24 is positioned so that a magnetic field as illustrated in FIG. 12 of the drawings directs the field lines of flux 52 perpendicular to lumen 34. Since this magnetic field 52 is perpendicular to the flow of blood through lumen 34, an induced voltage is generated, then detected by male terminals 27a and 27b which also are perpendicular to the flow of blood through central portion 43 of lumen 34. As noted, these terminals are also perpendicular to the direction of the field flux lines of magnetic field 52.

Thus, it will be apparent that as blood flows from tube 49 through the sensor 24 and out tube 39, the blood will be moving through an electromagnetic field focused by a focusing device 44 and generating an induced voltage which is sensed by male electrodes 27a and 27b. In the preferred embodiment of the invention, the electromagnetic field imposed on the blood flow is an alternating electromagnetic field with a constant amplitude which also is useful to eliminate polarization of the pickup electrodes. The conductive fluid velocity acted upon by the electromagnetic field generates a voltage proportional to the rate of flow of blood through the lumen 34. The male terminals 27a and 27b detect this induced voltage which can then be used as an indication of the rate of flow of blood through the lumen 34.

Next refer to FIG. 12 of the drawings which illustrates the electrical features and system employed in the invention. The sensor 24 directs blood through lumen 34 in the arrow direction 53 past terminals 27a and 27b. An electromagnet 48 directs a magnetic field 52 with field flux lines perpendicular to the arrow direction of the blood flow 53. The resulting flow voltage picked up by male terminals 27a and 27b is directed along lines 54 and 56 to an amplifier 57 which amplifies the voltage generated by the blood flow through magnetic field 52.

Terminals 27e are positioned in the body of sensor 24 as illustrated in FIGS. 3, 4 and 5 of the drawings and also in FIG. 2 of the drawings and provide a ground reference for the amplifier 57.

A power source 58 is connected to coil 59 which induces an electromagnetic field in the core of magnet 48 and thus induces an electromagnetic field 52 between poles 61 and 62 of the magnet 48. The induced electromagnetic force is directed by male terminals 27a and 27b to amplifier 57 where the induced voltage is amplified for further processing. This voltage is then fed from amplifier 57 to isolation transformer 63. Isolation transformer 63 is used so that dangerous currents cannot be circulated in the system. This type of isolation is necessary in typical biomedical circuitry in order to ensure safety for patients needing cardiovascular blood flow assistance. The output from the isolation transformer 63 is then fed to an integrator 64 where the signal is turned into a DC voltage directly proportional to the flow of blood through the lumen 34 of the sensor 24. The signal from integrator 64 is then directed to amplifier 66 which amplifies the signal to a high enough level to send a signal to display 67.

After the amplifier 66 moves the signal level, the voltage proportional to the flow velocity of the blood through the lumen 34 is sent to a scaled readout display 67 where the displayed numbers now correspond to the blood flow in liters per minute rather than volts. The display mechanism 67 can be any one of several types of display mechanisms which can express blood flow in terms of volume per unit of time. These include analog vane meters, digital numeric displays, digital bar displays and graphic cathodes ray tube displays. Liters per minute is one example of such display. Other volumetric flow rates may be displayed depending upon the desires of the operator of the system. In any event, the display 67 is a readout which displays the flow of blood through the tubes 49 and 51 in terms which are meaningful to the operator of the system and which are useful in determining the proper level of blood flow in the cardiovascular system of the patient.

Figure 13:
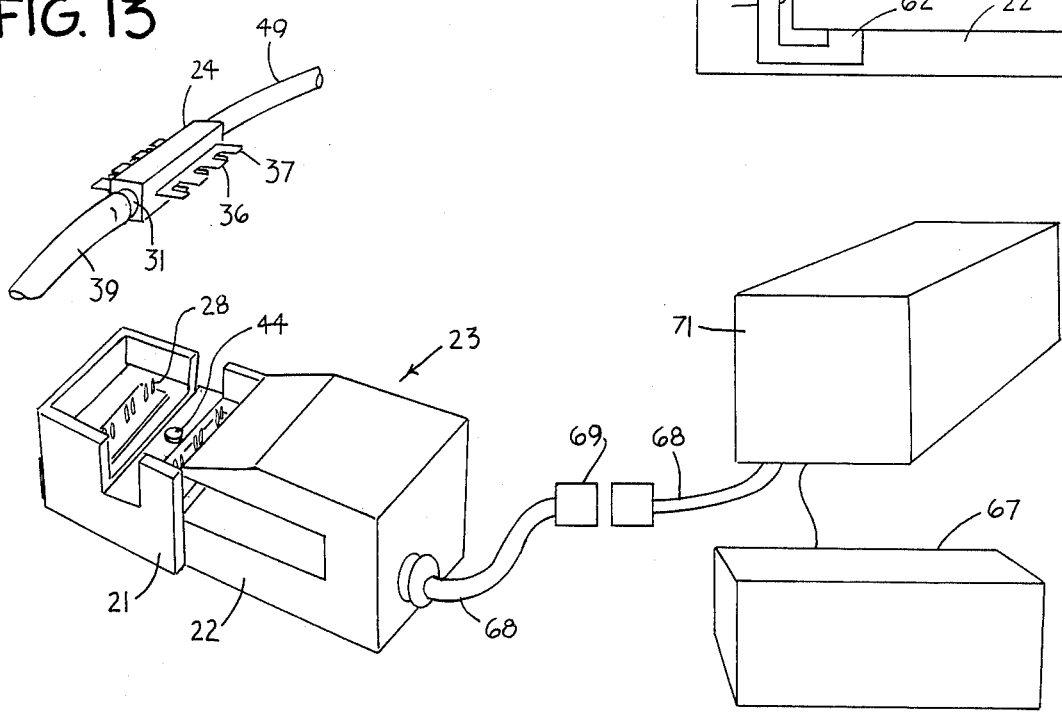
FIG. 13 is a block diagram illustrating the combination of mechanical and electrical features of the invention

An overall view of this electronic system and the sensor is illustrated in FIG. 13 of the drawings where the sensor 24 is illustrated in a partially exploded view showing the sensor 24 positioned to be engaged with the tray assembly 21 on slide 22. The transducer 23 is electrically connected via cable 68 to a connector 69. This cable 68 carries the electrical output from the transducer 23 which includes the electromagnet 48 through cable 68 to the electronics system 71 which incorporates amplifier 57, integrator 64 and amplifier 66. The output from his electronic circuitry 71 is fed to the display 67 where the flow of blood through sensor 24 can be expressed in analog or digital form if desired.

Refer next to FIGS. 16, 17 and 18 of the drawings. An important feature of the invention involves the control of an electromagnetic field 52 which is directed perpendicular to the blood flow in lumen 34 of the sensor 24. FIG. 16 illustrates a typical electromagnet having a field 52 which is energized by a coil 59. In the typical core 48, the electromagnetic field 52 has a curved shape as illustrated in FIG. 16. This magnetic field is not concentrated or controlled in any particular way and, consequently, the direction of the field lines of flux of such a magnetic field across the lumen 34 as illustrated in FIGS. 3, 4 and 5 of the drawings would provide a magnetic field which is relatively weak and uncontrolled. A feature of the invention is the employment of a focusing device 44 which will focus the field 52 so that the magnetic field 52 is more specifically focused across the lumen 34 at center section 43 of the lumen in order to generate a more precise and higher induced voltage.

In order to achieve this focused electromagnetic field which can be more readily sensed by male terminals 27a and 27b, the present invention employs a focusing device 44 which is illustrated in FIG. 17 of the drawings. Focusing device 44 is specifically adapted to engage core 42 as illustrated in FIGS. 3, 4 and 7 of the drawings. This core in one particular version is illustrated in FIG. 9 of the drawings where it is positioned in tray assembly 21 of the mechanism. This focusing device 44 is positioned between poles 61 and 62 and focuses the magnetic field 52 so that the magnetic lines of flux are more concentrated in the central portion 43 of the lumen 34.

The effectivenss of the focusing device 44 is illustrated in FIG. 17 of the drawings where it is noted that the field 52 is relatively undirected and the lines of magnetic flux are separated and unconcentrated. The effect of the focusing device 44 is to concentrate the field as illustrated in field 73 where the magnetic lines of flux 73 are more focused in a more parallel configuration. It is in this section 73 where the sensing device 24 is located and with the focusing device 44 positioned within cavity 42 of the body 32, the field 73 is more precisely directed over section 43 of the lumen 34. This focusing of the electromagnetic field 73 increases the intensity of the field and consequently increases the magnitude of the induced voltage generated by the flow of blood through, the lumen 34 as it passes through the intensified field 73 between poles 61 and 62.

In another variation of the invention, the magnetic focusing device 44 is permanently positioned in cavity 42 of the body 32 of sensor 24. This particular version of the invention is illustrated in FIG. 3 of the drawings where focusing device 44 is illustrated permanently embedded in the cavity 42.

Another variation of the invention is illustrated in FIG. 18 of the drawings in which there is illustrated two focusing devices 44. In this version, two focusing devices 44 are located in the magnetic field 52 in order to more precisely control the magnetic field of 52 between poles 61 and 62 of the magnet 48. In this particular variation of the invention, the one focusing device 44 may be positioned in the tray 21 with the second focusing device 44 positioned in transducer 23.

A further option is illustrated in FIG. 5 of the drawings where the sensing device 24 is illustrated with two cavities, 42 and 46, each of which is adapted to accommodate a magnetic field focusing device 44. In the illustration of FIG. 5 of the drawings, the focusing devices 44 are positioned along with the sensor 24 in the tray 21. When the sensor 24 is moved into engagement with the transducer 23, both focusing devices are moved into alignment with the magnetic field 52. Magnetic focusing devices 44 are positioned within cavity 42 and cavity 46 of the body 24 so that the electromagnetic field 52 is focused as illustrated in FIG. 18 in order to achieve a more precise focusing of the electromagnetic field 52 between poles 61 and 62. As previously indicated, it is desirable that the central field 72 be focused so that it encompasses the boundaries of central portion 43, see FIG. 3 of the drawings, of the sensing device 24.

An alternate version of this invention also includes the use of two focusing devices 44 as illustrated in FIG. 18 of the drawings In this version, two focusing devices 44 are utilized in a sensor as illustrated in FIG. 5 of the drawings might be employed in order to further control and intensify the magnetic field 72 directed perpendicular to the longitudinal axis 33 of the lumen 34. This particular version of the invention further intensifies the electromagnetic field 72 by focusing the field lines of flux of the magnetic field 72 to thereby increase the induced electromotive force caused by passage of the blood through the field 72 and, therefore, increase the magnitude of the voltage induced for sensing by the male terminals 27a and 27b.

Focusing devices 44 may be embedded in the cavities 42 and 46 of the body 32 of the sensor 24 or they may be positioned in the tray and transducer 23. Any combination of positioning of the focusing devices 44 may be utilized including employment of a single focusing device in the tray in combination with a focusing device 44 in the body of the sensor. An alternate embodiment, of course, could include the use of a focusing device in the transducer 23 and a focusing device mounted in the tray. Further, another combination might include a focusing device in the transducer with a second focusing device 44 embedded in a cavity 42 of the sensor 24. All of these various combinations are within the contemplation of this invention.

A further important feature of this invention is illustrated in FIGS. 14 and 15 of the drawings which illustrate differing cross-sectional views of the lumen 4, particularly the constricted central portion 43. The magnitude of the voltage which is induced as a result of blood flow through lumen 34 and specifically in the area of the central section of 43 can be illustrated by a formula as follows:

$$E = B \, V \, L.$$

In this formula, the induced voltage, measured in volts, is represented by E. B, measured in Gauss, equals the magnitude of the magnetic flux density through which blood flows. V, measured in meters per second, equals the average velocity at which the blood flows through the electromagnetic field B. L, measured in meters, is the length of the lumen through which the blood flows, measured between male terminals 27a and 27b. The directions of B, V and L are mutually orthogonal to maximize the magnitude of E.

It will be apparent from this formula that concentration of the electromagnetic field B will result in an increase in the induced electromotive force. Consequently, it is obvious at this point why the concentration devices 44 are effective in this particular invention since these focusing devices 44 focus or increase the lines of flux of the electromagnetic lines of force which are focused on central portion 43 of the lumen 34. Consequently, it will be apparent that increase of the flux lines or increase of the magnetic field B will result in a directly proportional increase in the electromotive force generated and which can be sensed by male terminals 27a and 27b.

By reducing the cross-sectional area of the lumen 34 in the area of central section 43, the velocity of the blood flow will increase in section 43. This principle is illustrated in FIG. 15 of the drawings where it is indicated that the lumen 34 is changed so that the input from nipple 29 has a cross-sectional area which is constricted by converging or focusing section 74 to reduce the cross-sectional area of the lumen 34 to a reduced cross-sectional area illustrated in FIG. 14 of the drawings. This reduced cross-sectional area in section 43 results in an increase in the velocity V of the blood flowing along the length Z through section 43 between boundaries 47 (FIG. 15) of the lumen 34. This increased velocity created by the focusing or constriction of the lumen 34 results in a further increase in the induced voltage generated as the blood flows through the electromagnetic field 73 or 72 as illustrated in FIGS. 17 and 18 of the drawings This increased velocity will increase the electromotive force generated and which can be detected by male terminals 27a and 27b as will be apparent by reference to the above-identified formula where electromagnetic field is directly proportional to the velocity of blood flow through the lumen 34.

It has also been found that the length L of the central cross-section 43 is also directly related to the induced voltage. As the length L is made greater or as male terminals 27a and 27b are moved further apart, the conductor length L becomes greater with the result that a greater voltage is generated as blood flows through the central section 43 of the lumen 34. Note that terminals 27a and 27b are separated by the distance of the length L of the long side of the constricted or central section 43 of the lumen. If the constricted section 43 is an ellipse, the length L would be the long axis of the ellipse. Consequently, reduction of the cross-section of central section 43 by increase o the length L and a reduction of the width W of the cross-sectional area of center section 43, as illustrated in FIG. 14 of the drawings, will further increase the electromotive force generated.

In terms of hydrodynamic flow, the greatest pressure $P_1$ occurs at the input or through tube 49 (see FIG. 10 of the drawings) where blood flows into the lumen 34 of the sensor 24. In the focusing or converging section 74, the lumen 34 is constricted and reduced in cross-sectional area to a cross-section illustrated in FIG. 14 of the drawings. Refer also to FIG. 19 of the drawings where the converging area section or 74 of the lumen 34 is illustrated in prospective. In this FIG. 19, it is apparent that the total cross-section of the lumen 34 is reduced from the circular cross-section illustrated in nipple 29 to a substantially reduced cross-section in central section 43.

The constriction illustrated in focusing section 74 is preferably focused at a rate which is illustrated by angle A of FIG. 5 of the drawings. Angle A is determined by the requirements of flow dynamics and preferably angle A is no greater than 5 degrees relative to the longitudinal axis 33 of lumen 34. An angle of 2.5 degrees has been found to provide near optimum function. These choices of angles will tend to reduce turbulence which tends to cause blood damage. A greater constriction of the blood flow tends to cause turbulence which may interfere with the accurate measurement of the generated voltage in section 43.

After the blood flow has been focused through section 43 and it passes by male terminals 27a and 27b, the blood flow is then again directed into a divergent or output section 76 of a lumen 34 where it is then permitted to flow out of the sensor 24 through nipple 31 having a lumen 34 which is the same as the input nipple 29. Again, the divergent section 76 has an angle of divergence which is consistent with fluid flow requirements but may have a divergence angle A of 5 degrees or less in order to reduce the turbulence in the fluid flow and, thereby, reduce or minimize the damage to blood as the blood is focused and diverged through central or constricted section 43 of the lumen 34.

It is specifically noted that the blood flows from a position of relatively high pressure $P_1$ through the converging section 74 and into the central or constricted section 43 where the velocity increases as a result of reduced cross-sectional area of the lumen 34. The blood then is exposed to a divergent section 76 where the blood returns to the normal and larger cross-sectional portion of lumen 34. The pressure P0 in this section is slightly lower than $P_1$. It is indicated that the lowest liquid pressure on the blood is experienced in the flow through the central portion 43 where the induced voltage is generated and detected by male terminals 27a and 27b.

The important feature of the constriction of the lumen 34 involves the reduction of the cross-sectional area 77 of the lumen 34 in order to increase the velocity of the blood flow. This increased velocity operates the same as an increase in the rate of movement of a conductor through a magnetic field. The resulting increase in velocity in accordance with the above-identified formula increases the magnitude of the induced voltage which can be detected. The cross-sectional area 77 is preferably ellipse 40 or rectangular in shape, the rectangular shape being as illustrated in FIG. 14 of the drawings in solid lines. However, other shapes may be employed, including modified elliptical or rectangular shapes and other shapes. The important feature of the cross-sectional dimension is to maintain the length L larger than the width W in order to amplify the induced voltage in the terminals 27a and 27b. An elliptical shape has the added advantage over a rectangular shape of maintaining a length L equal to the length L of the rectangle but for equal width W would further reduce the cross-sectional area and further increase the velocity at which the blood flows through the lumen 34.

Thus, it will be apparent that utilization of a cavity 42 in order to accommodate a focusing device 44 will enhance the electromotive force detectable by male terminals 27a and 27b because the focusing device 44 will focus the electromagnetic field between poles 61 and 62 of core 48 in order to elevate or increase the induced voltage generated. Since the induced voltage is generated at a higher level, the increased electrical signal can be more easily detected. Since a greater magnetic force is induced by the utilization of the sensor 24, having the reduced cross-sectional area in central section 43, blood flows in tubes 29 and 31 which are normally relatively low can be detected with greater precision.

The added benefit of using the focusing device 44 also intensifies the voltage signal which is generated as a result of blood flow through the electromagnetic field 73 and 72 with a result that very low blood flow can be detected with increased accuracy. This can be a significant advantage during surgical procedures since a patient's blood flow may be very low. This device, nevertheless, is capable of measuring low blood flow rates, displaying and alerting surgical teams of the relatively low blood flow. In practice, the device has been able to detect and display blood flows in the region of one (1) to four (4) milliliters per minute.

An additional feature of this device includes the feature that the sensor 24 can be made to be a disposable type sensor which can be discarded after each surgical procedure and, therefore, insuring sterility of the blood flow system. The sensor 24 may simply be discarded from the system and a new blood flow device 24 can be employed with the transducer 23 and slide tray 21. This disposable sensor 24 permits the transducer 23 and the slide 21 to be reused with the disposal of a relatively inexpensive sensor 24. From the above description, it will be apparent that the indicated sensor assembly will provide a method for employing a sensing device for a blood flow measuring system which insures sterility. The sensor 24, as devised, insures that the blood flow system is isolated from the electrical detection system and, thereby, insures that the patient has a sterile system for circulating blood while the electronic system can be reused without disposal. The sensor is relatively inexpensive as compared to the transducer 23 and tray 21 and, therefore, disposal is of little economic consequence and can be readily replaced.

The above description is only illustrative of the features of the invention and is not to be construed as limiting. As an example, the disposable device 24 can be employed with a variety of locations of the focusing device 44. Such focusing devices can be located in either the sensor 24 itself or in the tray 21 and/or a transducer 23. Combinations of these locations are within the contemplation of this invention. The cross-sectional area of section 43 of the invention can be varied dramatically. Such cross-sectional areas include that of the rectangular shape as illustrated in FIG. 14 of the drawings, but also can include oval and similar shapes of cross-sectional areas. The important feature, however, is that the length L of the cross-sectional area is greater than the width W.

What is claimed:

1. A blood flow meter system comprising:
   a. a transducer means;
   b. a tray means;
   c. first electrical terminal means mounted in said tray means;
   d. magnetic field generating means mounted in said transducer means for generating a magnetic field;
   e. said magnetic field generating means including an electromagnet means mounted in said transducer means with poles of said electromagnetic means terminating at opposite sides of an opening in said transducer means;
   f. said tray means adapted to move into engagement with said transducer means in said opening to position said first electrical terminals means generally between the poles of said electromagnetic means;
   g. means for activating said generating means to generate a magnetic field between the poles of said electromagnetic means;
   h. a disposable sensor means constructed of nonmagnetic and non-conductive material having a constricted section of lumen adapted to accommodate blood flow;
   i. second electrical terminal means mounted in said sensor means perpendicular to the flow of blood through said sensor means and in communication with said constricted section of lumen;
   j. said sensor means positioned in said tray means with said second terminal means in electrical contact with said first electrical means;
   k. a first electromagnetic field focus means positioned within the electromagnetic field between the poles of said electromagnetic means and in alignment with the constricted section of lumen of said sensor means to focus said electromagnetic field perpendicular to said blood flow in said constricted section of lumen of said sensor means to amplify the electromagnetic field intensity; and
   l. detection means connected to said second terminals for detecting the voltage induced by said flow of blood through said electromagnetic field.

2. A system in accordance with claim 1 which further includes a second electromagnetic field focus means positioned within the electromagnetic field between the poles of said electromagnetic means and positioned to cooperate with said first electromagnetic field focus means to focus said electromagnetic field.

3. A system in accordance with claim 1 in which said first electromagnetic focus means is mounted on said tray means.

4. A system in accordance with claim in which said first electromagnetic focus means is mounted on said transducer.

5. A system in accordance with claim 1 in which said sensor means has a cavity and in which said first electromagnetic field focus means is positioned in said cavity.

6. A system in accordance with claim 2 in which said first electromagnetic field focus means is mounted in said transducer and in which said second electromagnetic field focus means is mounted in said sensor means.

7. A system in accordance with claim 2 in which said first electromagnetic field focus means is mounted in said transducer and in which said second electromagnetic field focus means is mounted in said tray means.

8. A system in accordance with claim 2 in which said sensor means has a cavity and in which said first electromagnetic focus means is positioned in said cavity and in which said second electromagnetic focus means is positioned in said tray means.

9. A system in accordance with claim 2 in which said sensor means has first and second cavities in alignment with said magnetic field and in which said first and second electromagnetic focus means and positioned in said first and second cavities.

10. A system in accordance with claim 1 in which said constricted cross-sectional area has a cross-sectional length greater than the cross-sectional width and in which said second electrical terminal means are mounted at the extremity of said length of said cross-sectional area.

11. A system in accordance with claim 10 in which said cross-sectional area is the shape of an ellipse.

12. A system in accordance with claim 10 in which said cross-sectional area is the shape of a rectangle.

13. A system in accordance with claim 1 in which said lumen has an input section and an output section, said input section connected to said constricted section by a converging section and said constricted section connected to said output section by a diverging section.

14. A system in accordance with claim 13 in which said converging section converges with said constricted section at an angle of no greater than 5 degrees relative to the longitudinal axis of said lumen.

15. A system in accordance with claim 13 in which said converging section converges with said constricted section at an angle of no greater than 5 degrees relative to the longitudinal axis of said lumen and in which said diverging section diverges from said constricted section at an angle of no greater than 5 degrees relative to the longitudinal axis of said lumen.

16. A system in accordance with claim 13 in which said converging section converges with said constricted section at an angle of no greater than 2.5 degrees relative to the longitudinal axis of said lumen.

17. A system in accordance with claim 13 in which said converging section converges with said constricted section at an angle of no greater than 2.5 degrees relative to the longitudinal axis of said lumen and in which said diverging section diverges from said constricted section at an angle of no greater than 2.5 degrees relative to the longitudinal axis of said lumen.

18. A system in accordance with claim 1 in which said sensor means has a cavity located adjacent said constricted section area in said electromagnetic field.

19. A system in accordance with claim 18 in which the dimension of said cavity perpendicular to the blood flow in said lumen is greater than the length of the cross-sectional area of said constricted cross-sectional area.

20. A system in accordance with claim 19 in which said cavity is the form of a cylinder and the cavity is positioned in said sensor means with the central axis of said cavity perpendicular to said blood flow in said lumen.

21. A disposable blood flow sensor for a magnetic blood flow system employing a magnetic field between a pair of magnetic poles which comprises a body portion constructed of non-magnetic and non-conductive material, said body portion having a lumen extending along a longitudinal axis of said body portion from an input section to an output section to direct blood through said body portion, said lumen having a constricted section intermediate said input section and output an electromagnetic field focus means associated with said body portion and in alignment with the constricted section of lumen, said sensor being positioned between said magnetic poles with said constricted section of said lumen intersecting said magnetic field and a pair of electrical terminal means mounted in said body portion and communicating with said constricted section of said lumen to detect an electromotive force generated by the flow of blood in said lumen through said magnetic field.

22. A sensor in accordance with claim 21 in which said constricted section has a cross-sectional area with a length greater than the cross-sectional width.

23. A sensor in accordance with claim 22 in which said cross-sectional area is the shape of an ellipse.

24. A sensor in accordance with claim 22 in which said cross-sectional area is the shape of a rectangle.

25. A sensor in accordance with claim 21 in which said lumen has a converging section which interconnects said input section and said constricted section and which further includes a diverging section interconnecting said constricted section and said output section.

26. A sensor in accordance with claim 25 in which said converging section converges with said constricted section at an angle of no greater than 2.5 degrees, relative to the longitudinal axis of said lumen.

27. A sensor in accordance with claim 25 in which said converging section converges with said constricted section at an angle of no greater than 2.5 degrees relative to the longitudinal axis of said lumen and in which said diverging section diverges from said constricted section at an angle of no greater than 2.5 degrees relative to the longitudinal axis of said lumen.

28. A sensor in accordance with claim 25 in which said converging section converges with said constricted section at an angle of no greater than 5 degrees relative to the longitudinal axis of said lumen.

29. A sensor in accordance with claim 25 in which said converging section converges with said constricted section at an angle of no greater than 5 degrees relative to the longitudinal axis of said lumen and in which said diverging section diverges from said constricted section at an angle of no greater than 5 degrees relative to the longitudinal axis of said lumen.

30. A sensor in accordance with claim 21 which further includes a cavity in said body portion positioned in a location of said body portion adjacent said constricted section and a magnetic field focus means mounted in said cavity to focus said magnetic field when said body portion is positioned in said magnetic field.

31. A sensor in accordance with claim 21 which further includes first and second cavities in said body portion, each of said cavities positioned on opposing sides of said body portion and on opposing sides of said constricted section, and in which said focus means includes magnetic field focus devices mounted in each of said first and second cavities to focus said magnetic field when said body portion is positioned in said magnetic field.

32. A sensor in accordance with claim 21 in which said constricted cross-sectional area has a cross-sectional length greater than the cross-sectional width and in which said electrical terminal means are mounted at the extremity of said length of said cross-sectional area.

33. A sensor in accordance with claim 32 in which said cross-sectional area is the shape of a rectangle.

34. A sensor in accordance with claim 32 in which said cross-sectional area is the shape of an ellipse.

35. A sensor in accordance with claim 30 in which the dimension of said cavity perpendicular to the blood flow in said lumen is greater than the length of the cross-sectional area of said constricted cross-sectional area.

* * * * *